(12) United States Patent
Paulen et al.

(10) Patent No.: US 8,758,329 B2
(45) Date of Patent: Jun. 24, 2014

(54) LIQUID CATHETER, PARTICULARLY A URINARY CATHETER, METHOD AND DELIVERY DEVICE

(75) Inventors: Thomas Gijsbert Paulen, Eindhoven (NL); Lambertus Hubertus Bartholomeus Bemelmans, Amsterdam (NL)

(73) Assignee: IQ+ Investments N.V., Curacao (AN)

( * ) Notice: Subject to any disclaimer, the term of this patent is extended or adjusted under 35 U.S.C. 154(b) by 197 days.

(21) Appl. No.: 12/739,178

(22) PCT Filed: Oct. 22, 2008

(86) PCT No.: PCT/NL2008/050664
§ 371 (c)(1),
(2), (4) Date: Sep. 2, 2010

(87) PCT Pub. No.: WO2009/054720
PCT Pub. Date: Apr. 30, 2009

(65) Prior Publication Data
US 2010/0324540 A1    Dec. 23, 2010

(30) Foreign Application Priority Data

Oct. 22, 2007 (NL) .................................... 1034562

(51) Int. Cl.
*A61M 27/00*    (2006.01)
*A61M 25/00*    (2006.01)
A61M 25/01    (2006.01)
A61M 29/02    (2006.01)

(52) U.S. Cl.
CPC ......... *A61M 25/0017* (2013.01); *A61M 27/008* (2013.01); *A61M 25/002* (2013.01); *A61M 25/0067* (2013.01); *A61M 25/0111* (2013.01); *A61M 25/01* (2013.01); *A61M 29/02* (2013.01); *A61M 2210/1085* (2013.01); *A61M 2210/1089* (2013.10); *A61M 2210/1092* (2013.01); *A61M 2025/0175* (2013.01); *A61M 2202/0496* (2013.01)
USPC ........... 604/544; 604/540; 604/327; 604/328; 604/329

(58) Field of Classification Search
CPC .......... A61M 25/0017; A61M 25/002; A61M 25/005; A61M 25/0067; A61M 25/007; A61M 25/0074; A61M 25/04; A61M 25/0111; A61M 27/008; A61M 29/02; A61M 2210/1089; A61M 2210/1085; A61M 2025/0024; A61M 2025/0175; A61M 25/0662; A61M 2202/0496
USPC ........ 604/540, 544, 93.01, 95.01, 96.01, 104, 604/105, 106, 107, 158, 159, 160, 161, 604/164.01, 171, 172, 264, 265, 275, 533, 604/534, 535, 536, 327, 328, 329, 330; 600/30
See application file for complete search history.

(56) References Cited

U.S. PATENT DOCUMENTS

| | | | |
|---|---|---|---|
| 3,894,540 A * | 7/1975 | Bonner, Jr. .................... | 604/171 |
| 4,932,938 A | 6/1990 | Goldberg et al. | |
| 4,973,301 A | 11/1990 | Nissenkorn | |
| 5,176,664 A | 1/1993 | Weisman | |
| 5,242,398 A * | 9/1993 | Knoll et al. .............. | 604/103.05 |
| 5,322,501 A * | 6/1994 | Mahmud-Durrani ............. | 604/8 |
| 5,472,428 A * | 12/1995 | Peters ........................... | 604/171 |
| 5,518,498 A | 5/1996 | Lindenberg et al. | |
| 5,766,209 A * | 6/1998 | Devonec ......................... | 604/8 |
| 5,885,258 A * | 3/1999 | Sachdeva et al. ............. | 604/530 |
| 6,589,228 B2 * | 7/2003 | Holzer ........................ | 604/544 |
| 6,852,105 B2 * | 2/2005 | Bolmsjo et al. .............. | 604/544 |
| 6,855,126 B2 | 2/2005 | Flinchbaugh | |
| 2001/0044595 A1 | 11/2001 | Reydel et al. | |
| 2002/0072788 A1 * | 6/2002 | Hammond et al. .......... | 623/1.11 |
| 2004/0097891 A1 | 5/2004 | Bolmsjo | |
| 2004/0181235 A1 * | 9/2004 | Daignault et al. ............ | 606/108 |
| 2004/0243104 A1 * | 12/2004 | Seddon ........................ | 604/540 |
| 2005/0215980 A1 * | 9/2005 | Liu ................................ | 604/540 |
| 2006/0009859 A1 * | 1/2006 | Rioux et al. ................ | 623/23.66 |
| 2006/0111691 A1 * | 5/2006 | Bolmsjo et al. ............... | 604/544 |

FOREIGN PATENT DOCUMENTS

| WO | 82/03557 | 10/1982 |
| WO | 87/05523 | 9/1987 |
| WO | 00/21462 | 4/2000 |
| WO | 2006/055847 | 5/2006 |
| WO | 2007/043940 | 4/2007 |

OTHER PUBLICATIONS

International Search Report dated Oct. 6, 2009, from corresponding PCT application.

\* cited by examiner

*Primary Examiner* — Adam Marcetich

(74) *Attorney, Agent, or Firm* — Young & Thompson

(57) ABSTRACT

A liquid catheter, in particular a urinary catheter, includes a catheter shaft part (21) with a longitudinal liquid channel extending between a proximal and distal side thereof, and an anchoring body (22). The catheter body is intended to be received fully internally in a body cavity, such as in particular the urine bladder (50), and to drain the bladder from inside via the urethra (51). The catheter body has a length to span a distance between the bladder and a closure point (35) of the sphincter urethrae. An operating member (24,25) is connected durably to the catheter body to enable a user to carry the catheter body transluminally out of the bladder past the closure point. An insertion device for the catheter includes an insertion sleeve which can be carried transluminally as far as the urine bladder and from which the catheter body can be carried into the bladder.

25 Claims, 5 Drawing Sheets

LIQUID CATHETER, PARTICULARLY A URINARY CATHETER, METHOD AND DELIVERY DEVICE

The present invention relates to a liquid catheter, in particular a urinary catheter, comprising a catheter body which comprises a shaft part with a longitudinal liquid channel which is intended and adapted to allow a liquid flow between a distal side and a proximal side thereof, and an anchoring body on the distal side of the shaft part which is able and adapted to take on a relatively slender state in order to be received transluminally in this state in a body cavity of a patient, in particular a urine bladder, and to take on a transversely expanded state in order to prevent an unintended escape of the catheter body from the body cavity. The invention also relates to an insertion device and to a method for self-catheterization of a urine bladder with a catheter, wherein the catheter comprises a catheter body which is provided with at least one longitudinal liquid channel for guiding a liquid flow from a distal outer end to a proximal outer end thereof, and wherein the catheter body is at least partially introduced transurethrally into the urine bladder.

It is otherwise noted that within the scope of the present invention the terms "proximal", "distal" and conjugations thereof indicate positions which are related to an external environment of the user of the catheter. A proximal outer end is thus the outer end which is directed toward the user at first use and will be handled by him/her, while the distal side refers to the opposite side, in this case remote from the user, with which the catheter is inserted transluminally into the body of the user.

Urinary catheters are mainly applied for the purpose of catheterizing the bladder, wherein the bladder of a patient is drained by means of the catheter. Such a catheterization is important in patients who are bedridden or otherwise insufficiently able to go to the toilet normally, but also provides a solution for people who go without a toilet in certain circumstances, such as pilots and race drivers. In addition, urinary catheters provide a solution for users coping with a bladder deficiency in the sense that the urine bladder is not autonomously able to build up sufficient pressure to overcome the closing force of the sphincter urethrae.

There are different types, shapes and sizes of urinary catheters. An important distinction is made here between so-called intermittent catheters and indwelling catheters. The first type is inserted before each urination and removed again afterward, while the latter type is intended to be worn by a user for a longer period for repeated use.

An intermittent catheter is generally not much more than a hollow tube which is introduced transurethrally with a distal tip into the urine bladder for effective drainage thereof via the open connection thus created through the sphincter urethrae. A drawback of this type of catheter is that the insertion thereof requires a certain degree of dexterity and is in any case an unpleasant and frequently painful experience which has to be repeated for each urination. All in all, a urination cycle hereby becomes a relatively time-consuming and unpleasant activity for the user, and is not exactly free of medical risk. Furthermore, such a catheter does not provide a solution for the stated users suffering from a bladder deficiency, particularly when they are travelling for longer period of time.

These drawbacks are partially obviated by an indwelling catheter since this requires less frequent replacement and is suitable for successive urinations. A known, if not the best known embodiment of such a urinary catheter is the so-called Foley catheter. An example of this type of urinary catheter is described in international patent application PCT/SE82/00124. This catheter comprises a shaft part in the form of a long thin tube with a somewhat rounded tip to allow easier insertion. Situated immediately below the tip is an inlet opening, followed by an anchoring body in the form of an inflatable balloon which surrounds the shaft part. After being inserted into the urine bladder via the urethra, sterile water or other suitable liquid is guided into the balloon via an inflation channel provided for this purpose in the shaft part in order to inflate the balloon. The balloon thus anchors the catheter in the bladder in order to prevent unintended escape thereof, while the shaft part protrudes through the sphincter urethrae to provide an open connection from the urine bladder to the outside via the inlet opening so that the bladder can be fully drained via a liquid channel provided for this purpose in the catheter shaft part.

Because such a catheter can drain liquid continuously, a proximal outlet thereof usually debouches in a collecting container, such as for instance a urine bag, which is worn on the body or in the clothing. If desired, a hydrophilic material can be applied in the collecting container to absorb the urine irreversibly, in combination with bactericide and deodorizing agents. After a determined indwelling time considered as safe, the liquid is evacuated from the balloon, after which the catheter can be removed and, if desired, exchanged.

Because such a catheter need not be inserted and removed for each urination, from this point of view it provides the user with a considerably higher degree of comfort. The insertion of such a catheter is usually more complex than of an intermittent catheter, and therefore requires the necessary skill. Furthermore, the insertion of an indwelling catheter generally involves a danger of infections occurring, so that the procedure must preferably be carried out in a sterile environment which, certainly outside a hospital, can seldom be guaranteed. The introduction of a Foley catheter is therefore deemed as an operation reserved for only a doctor or nurse. However, due to the durable operation of an indwelling catheter the user does not have to rely constantly on assistance from a doctor or nurse, whereby this type of catheter is therefore very popular in cases suitable for this type of catheter.

In contrast however, the constant presence of the catheter may cause irritations. Because of the durable nature of this type of catheter greater demands are therefore made of the profile, i.e. the outer diameter, thereof so as to prevent the urethra being stretched too much thereby, which could otherwise result in discomfort or even in serious complications. There is moreover a continuous, relatively open communication between the urine bladder and the external collecting container, and this forms a danger, not to be underestimated, of the development of bladder infection, infections of the urethra or even kidney disorders.

In order to obviate these drawbacks the American U.S. Pat. No. 6,855,126 describes an indwelling catheter comprising a shaft part with a magnetic valve therein and a specially formed anchoring body thereon. After being inserted the anchoring body can be manipulated from a compact first state to an expanded second state using a transluminal operating member especially adapted for the purpose and an elaborate system of screw threads. The operating member can then be removed in order to leave clear the whole shaft diameter for the purpose of the intended draining operation. For the same drainage capacity a shaft profile can thus suffice which is significantly smaller than in the case of a classic indwelling catheter in which an inflation channel is also provided. Finally, the magnetic valve avoids a constant open connection between a proximal outlet of the catheter, which protrudes externally for instance into a collecting container, and the internal distal side of the catheter, so as to prevent the introduction of contamination, bacteria and other micro-organisms. The valve opens automatically under the influence of urine pressure prevailing in the bladder and urine flow from the bladder, and closes itself when this flow ceases, i.e. when the bladder has been sufficiently emptied.

Although this catheter known from U.S. Pat. No. 6,855,126 hereby obviates a number of drawbacks of the classic Foley indwelling catheter, it still has the drawback that the constant presence of the shaft part in the urethra, although this is much thinner than in the classic indwelling catheter, can still cause irritations and infections. The autonomous drainage of this catheter also requires a proximal outlet to debouch in a collecting container, which must therefore be worn constantly and exchanged in good time.

The present invention has for its object, among others, to provide a liquid catheter, in particular a urinary catheter, an insertion device and a method which also obviate these drawbacks to at least significant extent.

In order to achieve the intended object a liquid catheter, in particular a urinary catheter, of the type stated in the preamble has the feature according to the invention that, proximally of the anchoring body, the catheter body has on the one hand a sufficient length to span a distance between the body cavity and a closure point of a luminal sphincter, that on the other hand the catheter body is able and adapted to be fully received in the body cavity, distally of the closure point, and that at least one operating member is connected durably to the catheter body, which operating member extends proximally from the catheter body and is intended and adapted to enable a user to carry the catheter body transluminally out of the body cavity past the closure point with at least the proximal side of the shaft part.

A maximum urethral closing pressure of the sphincter urethrae prevails at the position of said closure point. With the operating member proximally accessible to the user the catheter can be taken transluminally out of the body cavity past this closure point with at least the proximal outer end of the shaft part in order to overcome this pressure, wherein the longitudinal liquid channel in the catheter shaft part forms an open connection along which urine can leave the body cavity. As soon as the body cavity has thus been sufficiently drained, the catheter body is displaced from the urethra back inside the body cavity under the influence of for instance a resilience, or is driven back therein by the user, whereby the lumen will be closed again by the sphincter urethrae.

The invention thus provides a completely new approach to (self-)catheterization, wherein the catheter body lies enclosed, and is worn wholly internally, within the body cavity in wrest position. The catheter body is, at least in rest position, always situated here wholly within a sterile environment and only for evacuation of the body cavity is it manipulated transluminally in a proximal direction distally from the body cavity. Because the catheter body according to the invention, other than a conventional indwelling catheter, does not normally have a long dwell time in the urethra, the known urethral irritations or damage are moreover avoided.

For the purpose of an autonomous self-returning character a particular embodiment of the urinary catheter according to the invention has the feature that the anchoring body is resilient and widens gradually in distal direction on at least a side thereof directed toward the shaft part. When carried transluminally past the closure point, the widening part of the anchoring body will be pressed in counter to this resilience and thereby generate a returning force.

In a preferred embodiment the catheter according to the invention has the feature that the anchoring body has a relatively compact first state which allows a transluminal introduction and is able and adapted to take on an at least transversely expanded, at least substantially balloon-shaped second state in order to prevent escape from the body cavity. The catheter body can here be brought beforehand into the compact first state in order to enhance transluminal introduction while, once in the body cavity, the second state prevents an unintended transluminal escape of the catheter body.

A further preferred embodiment of the urinary catheter according to the invention is characterized here in that the anchoring body is self-expandable from the relatively compact first state to the expanded second state. Due to this self-expandable, resilient character the anchoring body requires no further means for the purpose of moving from the relatively compact first state to the expanded second state. The shaft part can hereby retain a relatively slender profile, which enhances transluminal introduction and evacuation of the catheter body. The resilient character of the anchoring body has the additional advantage that an unavoidable compression thereof when the catheter body is driven past the closure point brings about an outward driving counterforce toward the body cavity. When the operating member is released, the catheter body will thereby automatically return to its rest position, wholly within the body cavity.

A further preferred embodiment of the catheter according to the invention has the feature that the operating member engages on the catheter body in order to enable a user to bring the anchoring body from the expanded second state to an at least partially compressed third state, wherein the shaft part reaches beyond the closure point, which third state allows a transluminal removal of the catheter body. No further means are thus required for repeated catheterization and complete transluminal removal of the catheter body from the urethra after a period of time. The anchoring member can always be brought into the third state by means of the operating member in order to allow such an evacuation. The operating member here may or may not be the same as that with which the shaft part can be manipulated in the above described manner.

In a further preferred embodiment the indwelling catheter according to the invention has the feature that the anchoring body comprises at least one bi-stable knee lever construction with a stable starting position in the expanded second state of the anchoring body, and that the operating member engages on the anchoring body in order to cause the anchoring body, once a dead centre position has been overcome, to transform from the expanded second state to a relatively compact stable final position allowing a transluminal removal of the catheter body. The anchoring body can here take on a reversible, unstable transitional state if the catheter body is manipulated with the shaft part toward the closure point and transform to the stable third state when forced beyond the dead centre position. This transition can be felt as a bend and subsequently allows a full removal. Without such forcing the catheter body will on the other hand always be pressed back to the body cavity when the operating member is released and return to the stable second state. A particularly user-friendly indwelling catheter is thus realized which can, without further instruments, be operated as desired and, if desired, be completely removed by the user, for instance in order to be eventually exchanged after a determined period of wear considered to be safe.

A particular embodiment of the catheter according to the invention has the feature that the anchoring body comprises a number of linked resilient filaments which are connected to a shaft part outer end and which are mutually separated in a peripheral direction between a top and the shaft outer end by longitudinal incisions, which filaments are able and adapted to transform from a straightened first state to a longitudinally curved state. These are specifically resilient filaments which flex from an unstable straightened state to a stable curved state as soon as the filaments are released. In a further particular embodiment the catheter according to the invention is characterized here in that the filaments are formed integrally with the shaft part. Such filaments can for instance be released from a shaft part body with high precision by means of laser cutting or a similar process. In the compressed first state of the anchoring body the filaments lie straightened, optionally under tension, roughly in line with the shaft part so as to allow a transluminal displacement in the urethra. By bringing the filaments or allowing them to move to their curved state the anchoring body takes on an expanded second state. In a rest position of the catheter this second state will be maintained by the anchoring body in order to prevent an unintended escape of the catheter body from the body cavity.

The operating member can be embodied in different ways. In a particular embodiment the catheter is characterized in this respect in that the operating member comprises a pull member, in particular a pull cord. The catheter body can thus be pulled using the operating member in order to carry the catheter body transluminally past the closure point and, if desired, then remove it completely. The anchoring body is here sufficiently compressed or optionally even folds down to a relatively compact third state in order to allow such a removal.

A further particular embodiment of the catheter according to the invention has the feature that the operating member comprises a torsion member, in particular a torsion wire. The operating member thus not only allows the catheter body to be pulled, but the catheter body can also be rotated about a longitudinal axis thereof by twisting the operating member. It is thus possible to achieve that the expanded anchoring body nestles around the shaft part so as to thus take on a relatively compact state which allows a trouble-free transluminal removal of the catheter body.

During use the operating member in the catheter according to the invention is in principle the only physical connection between the urine bladder with the catheter body therein on the one hand and the exterior of the user on the other. This drastically reduces the chance of the entry of bacteria and other micro-organisms or contaminations when compared to classic indwelling catheters with a hollow shaft part which protrudes to the outside. In order to further suppress this bacterial short cut a preferred embodiment of the urinary catheter according to the invention has the feature that the operating member comprises a monofilament wire. Such a wire is manufactured integrally with a solid core and is not twined, so that there are no cavities or other spaces present in which microorganisms or contaminations can linger. Such a wire can moreover take a relatively thin form so that the overall outer surface area thereof is small.

The operating member can fulfil a multiple function, i.e. serve both to carry the catheter body past the closure point in order to drain the body cavity and to fully remove the catheter body transluminally. Such a multiple operation simplifies the design of the catheter but requires a certain dexterity and feel in the user so that the one function is not performed unwittingly with the same operating member while the other was intended. In order to avoid this latter, a further embodiment of the catheter according to the invention has the feature that a further operating member engages on the shaft part of the catheter body and, just as the first operating member, extends proximally relative to a proximal outer end of the shaft part. The catheter body thus has individual operating members for the purpose of different manipulations with the catheter body.

In order to prevent irritations or rejection symptoms in and around the body cavity, a further particular embodiment of the indwelling catheter according to the invention has the feature that the proximal end of the shaft part narrows gradually, and in particular is rounded. A strong or even sharp transition is thus prevented during an introduction of the shaft part from the body cavity into the lumen, which enhances comfort. In a further embodiment of the catheter according to the invention a gradual transition of the transverse dimensions is also provided for similar reasons between the shaft part and the anchoring member. In addition, use is preferably made in a further embodiment of at least an external surface of a biocompatible plastic for at least the greater part of the catheter body.

The invention further relates to a device for transluminal insertion of an indwelling catheter in a user-friendly and practical manner. According to the present invention such an insertion device comprises an insertion sleeve with a longitudinal cavity open on at least a distal side for receiving the catheter body for axial displacement therein, and a proximal push member which lies with a distal outer end in the longitudinal cavity against a base part of a shaft part of the catheter body, and which protrudes with a proximal outer end outside the insertion sleeve. Prior to the introduction thereof the catheter body is thus enclosed for axial displacement in the insertion sleeve and is brought together therewith substantially up to the body cavity. The catheter body can then be forced out of the insertion sleeve using the push body and move into the body cavity. The insertion sleeve is then removed together with the push member, wherein the catheter body remains in the cavity. The introduction of the catheter is thus not only exceptionally user-friendly and easy to perform by the user him/herself; the insertion sleeve moreover avoids contact with the catheter body so that this latter can be inserted clean and possibly even fully sterile.

A preferred embodiment of the insertion device has the feature here that the push member comprises a longitudinal body cavity open on at least a distal side for receiving an operating member of the catheter for axial displacement therein. The push member thus provides space for the operating member of the catheter which becomes available when the push member and the insertion sleeve are removed, but which is hygienically stowed away up to that point.

For the purpose of a particularly hygienic or even sterile insertion, a further preferred embodiment of the insertion device according to the invention has the feature that the insertion sleeve is received displaceably in a longitudinal cavity of a placing sleeve and that the placing sleeve is provided with ejection means which are able and adapted to act on the insertion sleeve in order to drive this latter distally out of the placing sleeve. The placing sleeve is here placed on or a little into a luminal outlet and the insertion sleeve is then pushed therefrom by means of the operating member. The insertion sleeve does not therefore have to be touched and remains as free as possible from bacterial contamination.

In order to enhance a sterile insertion a further preferred embodiment of the insertion device according to the invention has the feature that the placing sleeve comprises an antiseptic means, in particular an antibiotic gel or liquid, at least inside a distal outer end thereof. A quantity of this means can for instance be provided on a distal outer end of the placing sleeve so that the insertion sleeve passes therethrough before entering luminally. An antiseptic introduction is thus achieved and thus prevents internal infections. In order to prevent the means drying out, and otherwise also for a hygienic closure of the whole, a further preferred embodiment of the insertion device according to the invention has the feature that the placing sleeve can be closed at a distal outer end, in particular with a removable cap, film or plug.

In order to facilitate insertion of the insertion sleeve with the catheter body therein, a further preferred embodiment of the device according to the invention has the feature that the placing sleeve is provided at a distal outer end with positioning means narrowing toward the outer end. The positioning means here provide for a self-locating character of the placing sleeve so that it automatically centres directly in front of an exit of the urethra, and moreover ensure a certain widening of the urethral opening, which contributes further to the comfort of insertion of the catheter body. In a particular embodiment the device according to the invention is characterized here in that the positioning means comprise at least one transverse widening which extends from an outer periphery of the distal outer end of the placing sleeve and tapers down to a centre line of the placing sleeve over at least a distal side thereof. Such a narrowing widening can be formed integrally over a full periphery of the placing sleeve, or for instance comprise a number of discrete longitudinal fins or ribs which are distributed uniformly over the periphery and which each narrow toward an outer end.

Insertion comfort is further enhanced with a further particular embodiment of the device according to the invention, which is characterized in that at least the insertion sleeve follows a radius of curvature, particularly one which is adapted to a usual curvature of a urethra of a user. The insertion sleeve will thus be less likely to act on the urethral wall during introduction thereof into the urethra; thereby preventing possible damage thereto and a painful sensation. A certain radius of curvature moreover provides ergonomic advantages which enhance handling and operation of the device.

A particular preferred embodiment of the insertion device has the feature that the ejection means comprise an outer casing which encloses the placing sleeve at a proximal outer end in axially displaceable manner, and that the outer casing is able and adapted to act on a proximal outer end of the insertion sleeve in order to drive this latter distally outside the placing sleeve during an axial displacement of the outer casing over the placing sleeve. The insertion sleeve is thus wholly concealed in successively the outer casing and the placing sleeve. By carrying the outer casing over the placing sleeve in distal direction the insertion sleeve can be carried distally outside the placing sleeve over a corresponding distance and received transluminally in the urethra. Direct hand contact with the insertion sleeve can herein be avoided, whereby this procedure can be performed in completely hygienic manner and, if desired, by the user him/herself.

In a further particular embodiment the insertion direction is herein characterized in that the outer casing comprises on a proximal side an end wall with a bore in which the push body is displaceable. Once the insertion sleeve has been placed transluminally, the push member can thus be actuated from the proximal side in order to drive the catheter body distally out of the insertion sleeve. A more or less close fit of the push member in the bore here prevents the entry of micro-organisms or other form of contamination. The push member can optionally be enclosed by a hermetically sealing membrane which connects to a proximal end wall of the device to prevent any form of entry of substances foreign to the body.

For the purpose of economic manufacture and from an ergonomic viewpoint, a further particular embodiment of the device according to the invention has the feature that at least substantially all components thereof are manufactured from plastic, in particular a biocompatible plastic.

The above specified catheter and device according to the invention provides a wholly new approach in respect of urinary catheterization, wherein a drainage channel through the sphincter urethrae is provided from the inside instead of from the outside. A method for self-catheterizing of a urine bladder with a catheter, wherein a catheter body is introduced transurethrally at least partially into the urine bladder, is characterized for this purpose according to the invention in that the catheter body is carried fully into the urine bladder distally past a urethral closure point of the sphincter urethrae, that from the urine bladder the catheter body is manipulated with a proximal side thereof beyond the urethral closure point in order to evacuate liquid from the urine bladder via the at least one liquid channel of the catheter body, and that following said evacuation the catheter body is once again admitted fully into the urine bladder distally beyond the closure point. An exceptionally practical self-catheterization is thus possible which can be performed in completely sterile manner, i.e. from the inside, and partly for this reason considerably limits the chance of complications. The catheter body is here substantially always situated outside the urethra, so that irritation or damage to a wall thereof is prevented as far as possible.

A preferred embodiment of the method according to the invention has the feature here that the catheter body is carried proximally beyond the closure point counter to a resilience of an anchoring body thereof, and that the catheter body is released, once the urine bladder has been sufficiently evacuated, in order to have the catheter body once again take up a starting position located wholly within the urine bladder distally beyond the closure point.

The invention will now be further elucidated on the basis of an exemplary embodiment and an accompanying drawing. In the drawing.

The figures are otherwise purely schematic and not drawn to scale. For the sake of clarity some dimensions in particular may be exaggerated to a greater or lesser extent. Corresponding parts are designated in the figures with the same reference numeral.

Figure 1:
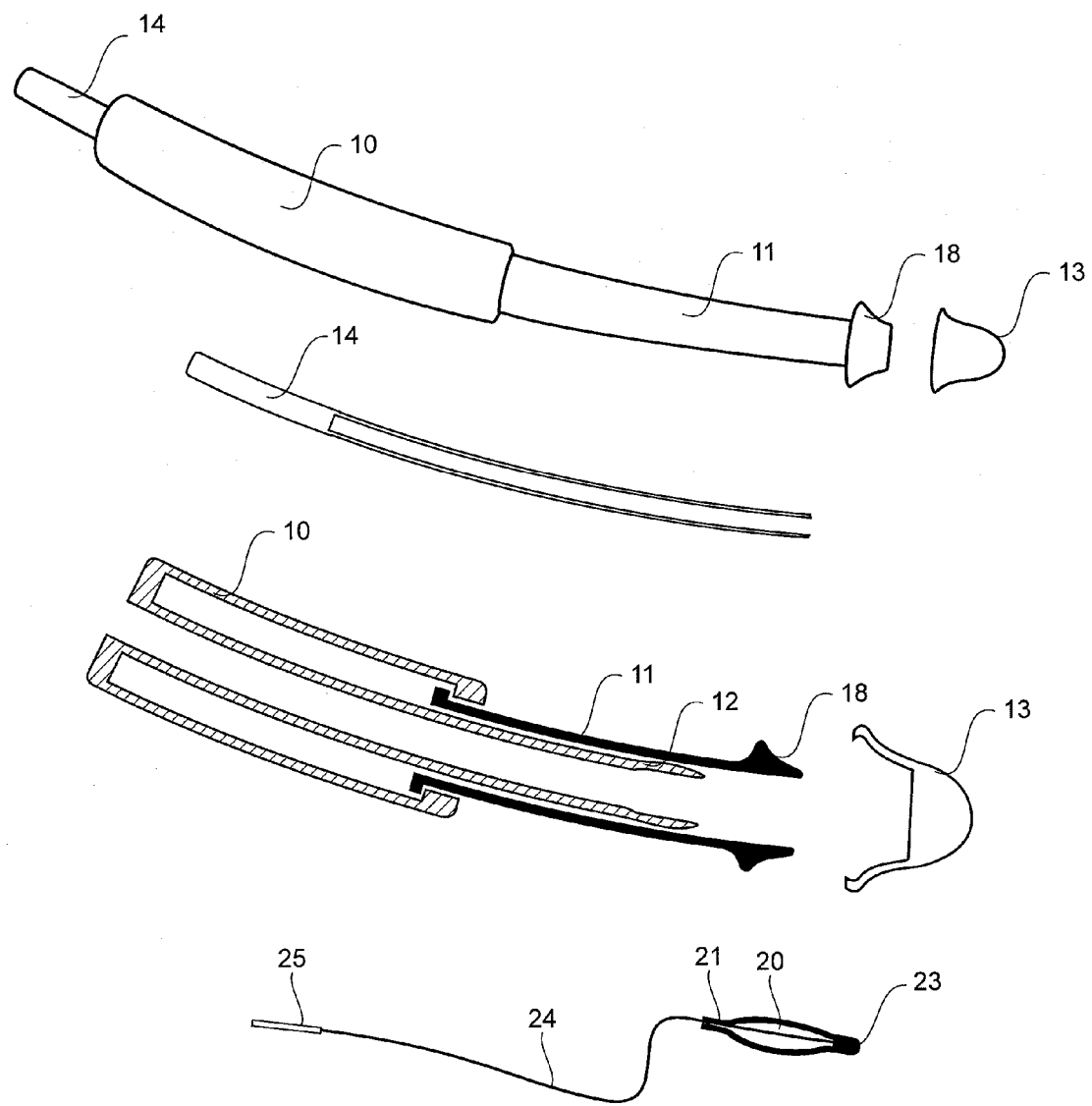
FIG. 1 shows an exemplary embodiment of an insertion device with a urinary catheter according to an exemplary embodiment of the invention as individual components.

The insertion device of FIG. 1 comprises an outer casing 10 which serves as a handle and which receives a placing sleeve 11 with a proximal side in axially displaceable manner. The parts of the insertion device are all manufactured from a biocompatible plastic in order to enhance acceptance in the body and to avoid irritations or even rejection. Placing sleeve 11 fully encloses the actual insertion sleeve 12, which thereby remains as free as possible from contamination. At a distal outer end the whole is sealed with a sealing cap 13 or other removable sealing means, such as for instance a removable plug or sealing foil. Optionally situated immediately in front of cap 13 or between insertion sleeve 12 and placing sleeve 11 is a quantity of antiseptic gel 15 or other antibiotic agent for maintaining a sterile environment. In addition, the gel fulfills a lubricating function when insertion sleeve 11 is inserted.

In order to achieve an accurate and user-friendly placing of placing sleeve 11 on a female urethral opening, positioning means narrowing toward the outer end are provided at the distal outer end of the placing sleeve in the form of a transverse widening 18 which extends from an outer periphery of the distal outer end of the placing sleeve over a whole periphery thereof and tapers down to a centre line of the placing sleeve over at least a distal side thereof. Instead of such an integral member it is also possible to opt for a number of discrete longitudinal fins which extend from an outer periphery of the distal outer end in uniformly distributed manner and narrow toward the outer end. On a distal side the widening 18 tapers down to a centre line of the placing sleeve and, when the placing sleeve is placed, thus centres the distal outer end thereof in front of the urethral opening, which is here also stretched slightly in order to allow a more comfortable introduction of the catheter to take place. Insertion sleeve 12 can thus exit distally from the placing sleeve in relatively unimpeded manner and enter the urethra transluminally. The urethral wall is thus spared as much as possible. The female urethra usually has a length of between 5 and 7 centimetres. The length of the insertion sleeve is adapted hereto.

Figure 2:
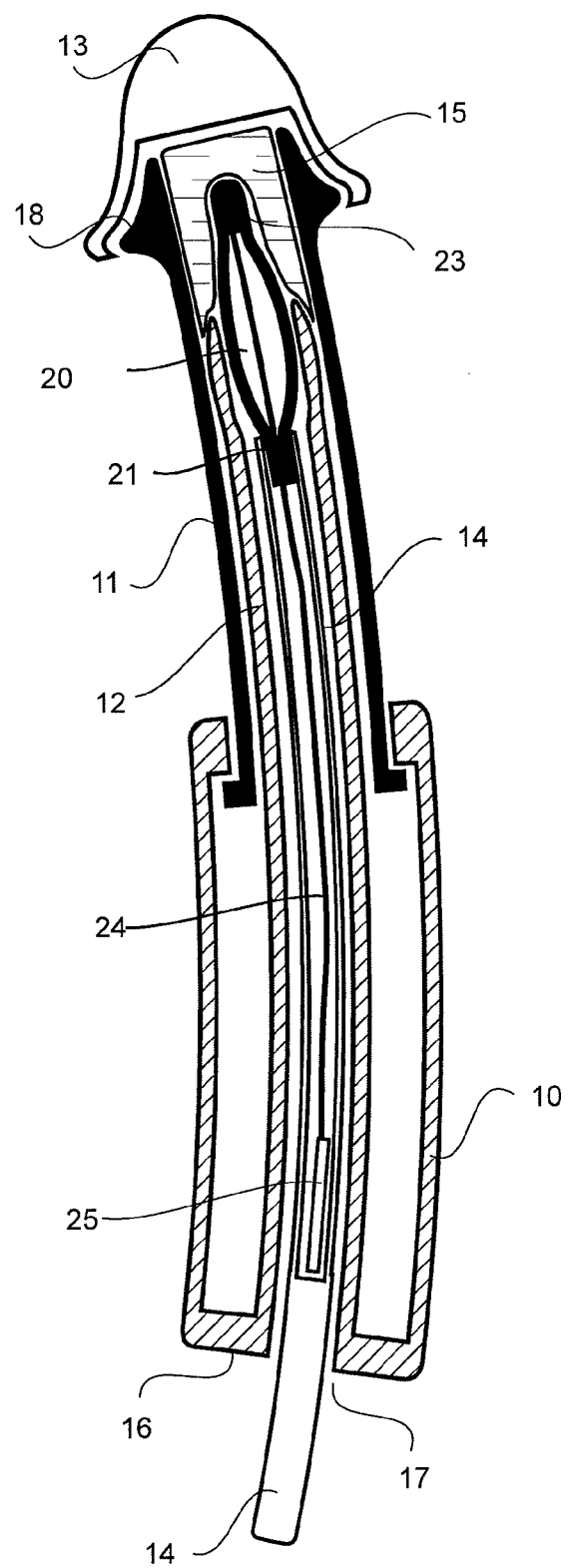
FIG. 2 shows a longitudinal section of the device with the catheter of FIG. 1 in assembled state.

At a proximal outer end the outer casing 10 comprises an end wall 16 having therein a bore 17 in which a push member 14 is close-fittingly displaceable, see also FIG. 2. In the assembled state, see FIG. 2, end wall 17 is connected to a proximal outer end of the insertion sleeve, so that there is a co-action therebetween for the purpose of driving the insertion sleeve distally out of the placing sleeve when the outer casing is displaced in a distal direction. Situated in turn in insertion sleeve 12 is the actual catheter 20-25 which, together with insertion sleeve 12 and push member 14, lies in a sterile part of the device surrounded by placing sleeve 11 and outer casing 10 which, together with the sealing cap, form on their outer side a non-sterile part of the device. Owing to this strict compartmentalization of the insertion device, it does not per se require a further, optionally sterile packaging.

A catheter body of the catheter comprises an anchoring body 20 between a tip 23 of the catheter and a catheter shaft part 21. Shaft part 21, catheter tip 23 and anchoring body 20 here form as integral whole the actual catheter body. Shaft part 21 is hollow along its full length in order to provide space for a longitudinal liquid channel which opens both proximally and distally inside anchoring body 20. Shaft part 21 thus provides a drainage channel along which liquid can drain away. An operating member 24 in the form of a pull cord with handle 25 is connected to the anchoring body to enable manipulation of the catheter body therewith once it has been inserted. Anchoring body 20 comprises a number of resilient filaments 22 which are mutually separated in a longitudinal direction by incisions. In the assembled state the filaments rest against an inner wall of insertion sleeve 12 counter to their resilience. Having moved out of this position, the filaments spring into an expanded rest position, see FIG. 3F, and thus impart more volume to the anchoring body.

Figure 3A:
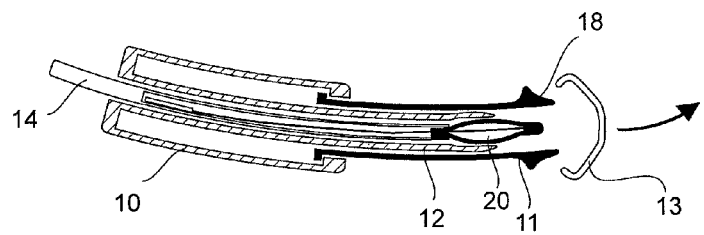
FIGS. 3A-3D show successive states of the insertion device and catheter of FIG. 1.
Figure 3B:
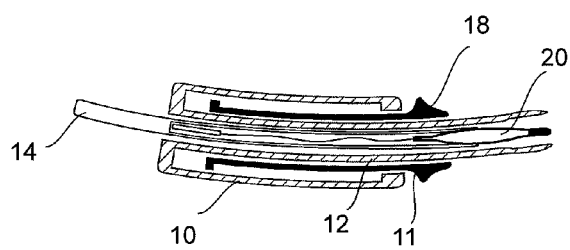
Figure 4A:
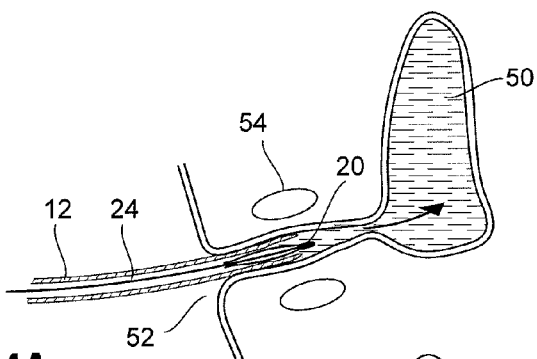
FIGS. 4A-4E show different stages of the use of the catheter of FIG. 1.

For optionally self-insertion of the catheter the sealing cap 13 is first removed, see FIG. 3A, and insertion device 12 is placed with the distal outer end of placing sleeve 11 against or a little into the urethral opening. Placing means 18 herein centre the whole a little inside the urethra. Outer casing 10 is then displaced with the handle in a distal direction roughly to the distal outer end of placing sleeve 11 in order to drive insertion sleeve 12 distally over a corresponding distance out of placing sleeve 11 and to carry it transluminally inside the urethra, see FIGS. 3B and 4A. The various components are dimensioned here such that a distal outer end of the insertion sleeve now lies substantially in front of or a little beyond an exit of a body cavity for catheterizing, in particular the urine bladder, see FIG. 4A. The insertion sleeve here follows a certain radius of curvature, indicated in the figures, which is adapted to a usual curvature of the female urethra so as to allow the introduction to take place as gradually as possible. The design of the placing sleeve and casing in this example are also adapted to give the whole a feminine character and to enhance the ergonomics of the whole.

Figure 3C:
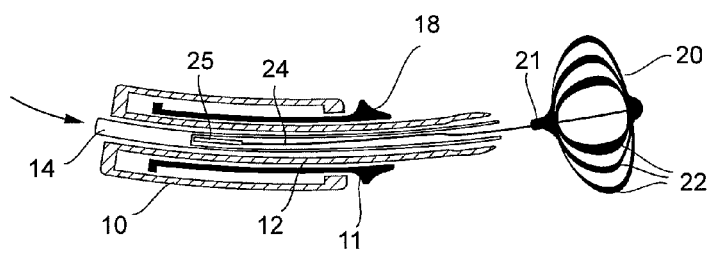
Figure 3D:
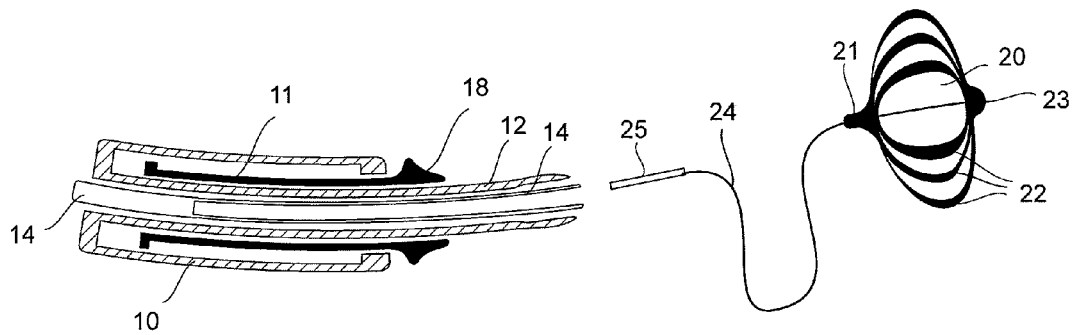
Figure 4B:
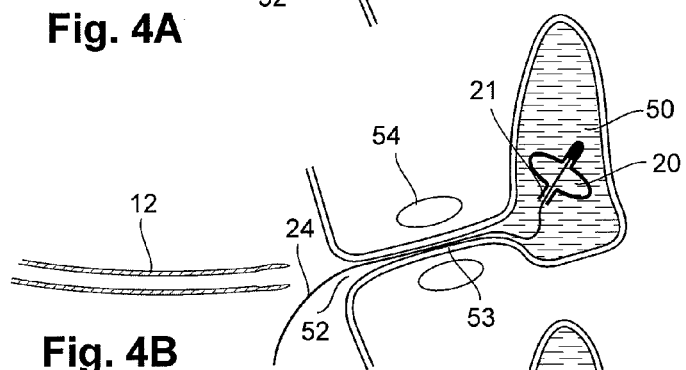

When insertion sleeve 12 has been inserted substantially fully into the urethra, push member 14 is pressed in for the purpose of driving catheter body 20-23 distally out of insertion sleeve 12, see FIGS. 3C and 4B. Due to the resilient nature of filaments 22 the anchoring body is self-expanding, whereby it transposes of itself from the compact state enclosed in the insertion sleeve to an expanded second state as shown in FIGS. 3C and 4B. In this state anchoring body 20 fixes catheter body 20-23 in the urine bladder so that the catheter body does not escape therefrom unintentionally. The insertion device is now retracted, see FIG. 3D, wherein catheter body 20-23 and pull cord 24,25 connected thereto remain behind in respectively the urine bladder and the urethra, see FIG. 4B. The pull cord is long enough to be reached externally.

FIG. 4B shows a rest position wherein catheter body 20-23 resides internally relatively freely inside body cavity 50. Catheter body 20-23 is here fully closed off from the outside world so that it does not allow passage for substances and micro-organisms foreign to the body. A sterile environment can thus be maintained for a long period of time. In order to enhance this further, use is made in this example for the operating member of a monofilament wire 24, for instance of a plastic such as polyamide (Nylon®) or polytetrafluoroethylene (Teflon®). Such a wire is not twined or otherwise wound, but has a completely flat and smooth outer surface to which bacteria or other micro-organisms cannot adhere, or hardly so.

Figure 4C:
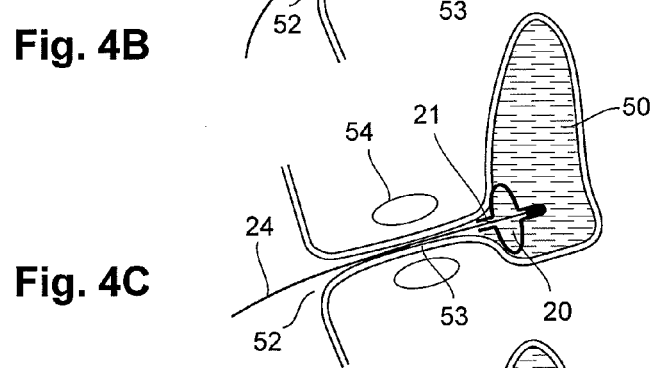
Figure 4D:
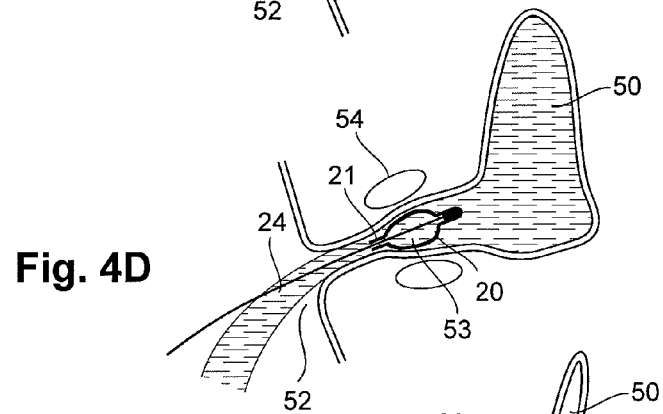

In order to evacuate liquid from body cavity 50 the catheter body is pulled in proximal direction out of cavity 50 inside urethra 52 using the pull cord, see FIG. 4C. The catheter body is pulled until a proximal side of shaft part 21 comes to lie beyond a closure point 53 of the urethra, see FIG. 4D. The urethra is here normally held closed by the sphincter urethrae 54 with the greatest pressure. This closure is now however opened by the cavity in shaft part 21, which provides an evacuation channel to urine from urine bladder 50 to urethral opening 52. The urine here exits into a toilet or, if desired, the urine is collected in a collecting member provided for this purpose.

Closure point 53 generally lies about halfway along the urethra, i.e. at a distance of about 2-3 centimetres from the urine bladder. A length of catheter body 20-23 is adapted hereto to enable spanning of this distance and thus provide an open urinary passage, while this length is on the other hand smaller than the internal size of the urine bladder so that in a rest position the catheter body lies received in the urine bladder in a manner which for a user is at least substantially wholly imperceptible and sterile. In this example use is thus made of a catheter body with a shaft part 21 of about 15-25 millimetres and with an overall length of about 40-60 millimetres in the expanded state and about 70-90 millimetres in the extended state. The anchoring body here widens gradually to a diameter of about 25-45 millimetres.

The displacement of catheter body 20-23 beyond closure point 53 takes place counter to the resilience of anchoring body 20. When pull cord 24 is released, the catheter body will thereby be pressed back automatically and once again take up its starting position in the urine bladder as shown in FIG. 4B. The catheter is now ready for a subsequent use.

Figure 4E:
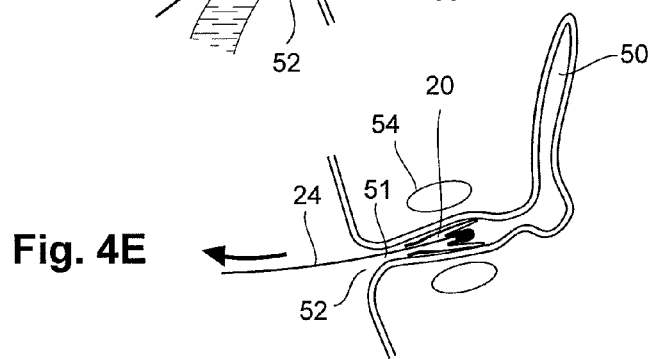

For definitive removal of the catheter body the pull cord 24 is pulled further until a bi-stable knee lever construction in filaments 22 is felt to fold down to the third state shown in FIG. 4E. Just as the rest state, this state is stable, although the profile of anchoring body 20-23 is here significantly more slender, which allows a transluminal removal when cord 24 is pulled all the way back. The catheter can now be discarded and, if desired, replaced with a new one. The catheter according to the invention can thus be worn safely and comfortably over a relatively long period of time and provides a solution particularly for users with a bladder deficiency whereby they are insufficiently able to develop a urine pressure autonomously which is sufficient to overcome the closing pressure of the sphincter urethrae.

Figure 5A:
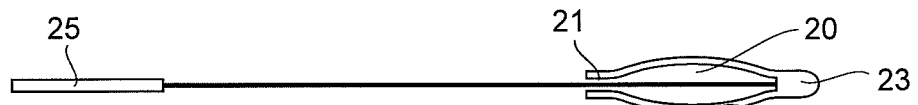
FIGS. 5A-5C show wholly schematic views of a first embodiment of a method for placing and operating a catheter according to the invention.
Figure 5B:
Figure 5C:

The different stages of insertion and operation of the catheter are again shown schematically in FIGS. 5A-5C. In the situation shown in FIG. 5A the catheter body is inserted to a position fully in the bladder cavity. If anchoring body 20 is self-expanding, it automatically springs into the transversely expanded state shown in FIG. 5B. It is also possible that the anchoring body is not self-expanding but only takes on such an expanded state after being brought manually into this state, for instance by pulling operating member 24,25 which in this case engages on a distal tip 23 of the anchoring body beyond filaments 22. The expanded state produces resistance which prevents the catheter body exiting the bladder and will bring about a returning force if the catheter body is nevertheless forced transluminally into the urethra by the user pulling the operating member. With an excessive pulling force the user will pull the anchoring body wholly past a closure point of the sphincter urethrae and the anchoring body folds down into the stable final position shown in FIG. 5C of a bi-stable knee lever construction present in filaments 22.

Figure 6A:
FIGS. 6A-6C show wholly schematic views of a second embodiment of a method for placing and operating a catheter according to the invention.
Figure 6B:
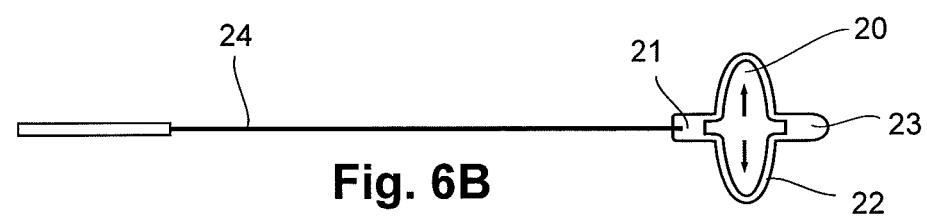
Figure 6C:
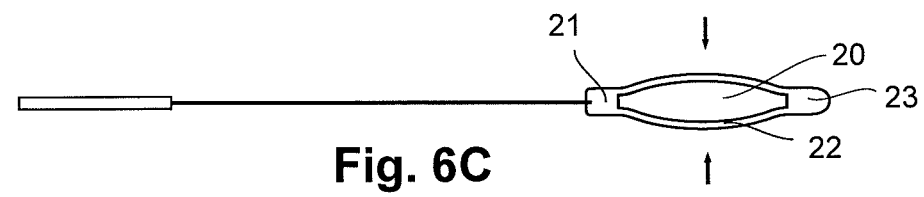

An alternative embodiment of arranging and manipulating a catheter according to the invention is shown schematically in FIGS. 6A-6C. Anchoring body 20,22 is here self-expanding, which means that it springs automatically from the compressed state shown in FIG. 6A to the state shown in FIG. 6B as soon as it is released. In the state shown in FIG. 6A the catheter body is enclosed in for instance a sleeve, wrapper or otherwise held forcibly in this state using fixation means in order to allow a transluminal introduction via the urethra. Once in the bladder cavity, the fixation means are removed and anchoring body 20,22 is released, whereby it springs into the state shown in FIG. 6B and prevents unintended exit of the catheter body from the bladder. The operating member is connected in this case to a proximal outer end of shaft part 21. If cord 24,25 is pulled, anchoring body 20,22 will be pulled transluminally into the urethra counter to its intrinsic resilience and manipulated into the state shown in FIG. 6C. Initially, this state will impose a returning force on the catheter body until anchoring body 20,22 is pulled roughly up to a position beyond a middle point thereof into the urethra. The urethra urges and then holds the anchoring body fully in the state shown in FIG. 6C in order to allow only a fully transluminal removal of the catheter body.

Although the invention has been further described on the basis of only a single exemplary embodiment, it will be apparent that the invention is by no means limited thereto. On the contrary, many more variations and embodiments are possible within the scope of the invention for the person with ordinary skill in the art. Instead of an optionally automatically fully expanding body it is thus also possible to apply an anchoring body which in a first state lies relatively flat in line with the shaft part and which is transversely or radially expanded in a second state, strictly speaking without thereby having increased in size.

The invention claimed is:

1. A liquid catheter, in particular a urinary catheter for insertion into a female bladder, comprising:
   a catheter body and at least one operating member extending proximally of said catheter body and being connected durably thereto,
   said catheter body comprising an elongated shaft portion having a longitudinal liquid channel for passing a liquid flow between a distal side and a proximal side thereof, and
   said catheter body comprising an anchoring portion distally of said shaft portion, said anchoring portion comprising an anchoring body which is deployable from i) a relatively slender first state, which allows a transluminal introduction of said catheter body in a user's body cavity defined by a female bladder, into ii) an expanded second state, which prevents an inadvertent escape of the catheter body from said body cavity defined by said bladder, said shaft portion having a sufficient length to reach beyond a closure point of a luminal sphincter while the anchoring body resides in said user's body cavity defined by said bladder, and said catheter body being sufficiently compact to be received completely inside said user's body cavity defined by said bladder,
   wherein the anchoring body is self expandable from said relatively slender first state into said expanded second state, wherein said anchoring body is balloon shaped in said expanded state and widens gradually in a distal direction at a side which is directed towards said shaft portion,
   wherein said anchoring body comprises a number of resilient filaments which are connected to said shaft portion and which are mutually separated in a peripheral direction by longitudinal incisions, which filaments are configured to transform from a straightened state to a longitudinally curved state and which filaments are configured and sufficiently resilient to expel said catheter body from said urethral sphincter and into said bladder in the absence of a force applied on said operating member.

2. The liquid catheter as claimed in claim 1,
   wherein the operating member engages on the catheter body to enable a user to bring the anchoring body from the expanded second state into an at least partially compressed third state in which the shaft portion reaches beyond the closure point,
   wherein said partially compressed third state is distinct form said relatively slender first state, and
   wherein said partially compressed third state allows a transluminal removal of the catheter body.

3. The liquid catheter as claimed in claim 2, wherein the operating member comprises a pull member that is engaged with a distal tip of the anchoring body enabling the user to bring the anchoring body from the expanded second state into the third state.

4. The liquid catheter as claimed in claim 1, wherein the anchoring body comprises at least one bi-stable knee lever construction with a stable starting position in the expanded second state of the anchoring body, and that the operating member engages on the anchoring body in order to cause the anchoring body, once a dead centre position has been overcome, to transform from the expanded second state to a relatively compact stable final position allowing a transluminal removal of the catheter body.

5. The liquid catheter as claimed in claim 1, wherein the filaments are formed integrally with the shaft portion.

6. The liquid catheter as claimed in claim 2, wherein the operating member comprises a pull member comprising a pull cord engaged with a distal tip of the anchoring body to enable the user to bring the anchoring body from the expanded second state into the third state.

7. The liquid catheter as claimed in claim 1, wherein the operating member comprises a torsion member, in particular a torsion wire.

8. The liquid catheter as claimed in claim 1, wherein the operating member comprises a monofilament wire.

9. The liquid catheter as claimed in claim 1, wherein a further operating member engages on the shaft portion of the catheter body and, just as the first operating member, extends proximally relative to a proximal outer end of the shaft portion.

10. The liquid catheter as claimed in claim 1, wherein the proximal end of the shaft portion narrows gradually, and in particular is rounded.

11. An insertion device comprising the liquid catheter according to claim 1, and further comprising:
an insertion sleeve with a longitudinal cavity open on at least a distal side, wherein said insertion sleeve accommodates the catheter body of the catheter inside said longitudinal cavity while allowing axial displacement therein; and
a proximal push member extending through said longitudinal cavity and lying with a distal outer end against the shaft portion of the catheter body,
wherein said push member protrudes with a proximal outer end outside the insertion sleeve over at least about a longitudinal length of an anchoring body of the catheter,
wherein said push member comprises a longitudinal body cavity open at least on a distal side, and
wherein the operating member of the catheter extends through said body cavity of said push member and is axial displaceable therein.

12. The insertion device as claimed in claim 11,
wherein the insertion sleeve is received displaceably in a longitudinal cavity of a placing sleeve, and
wherein the placing sleeve is provided with means for ejecting which are configured to act on the insertion sleeve in order to drive the insertion sleeve distally out of the placing sleeve.

13. The insertion device as claimed in claim 12, wherein the placing sleeve comprises an antibiotic gel or an antibiotic liquid, at least inside a distal outer end thereof.

14. The insertion device as claimed in claim 12, wherein the placing sleeve can be closed at a distal outer end with a removable cap, film or plug.

15. The insertion device as claimed in claim 12, wherein the placing sleeve is provided at a distal outer end with means for positioning that narrows toward the outer end.

16. The insertion device as claimed in claim 15, wherein the positioning means comprise at least one transverse widening which extends from an outer periphery of the distal outer end of the placing sleeve and tapers down to a centre line of the placing sleeve over at least a distal side thereof.

17. The insertion device as claimed in claim 12,
wherein the means for ejecting comprise an outer casing which encloses the placing sleeve at a proximal outer end in axially displaceable manner, and
wherein the outer casing is configured to act on a proximal outer end of the insertion sleeve in order to drive the latter distally outside the placing sleeve during an axial displacement of the outer casing over the placing sleeve.

18. The insertion device as claimed in claim 17, wherein the outer casing comprises on a proximal side an end wall with a bore in which the push body is close-fittingly displaceable.

19. The insertion device as claimed in claim 18, wherein the outer casing at least abuts with the end wall against a proximal outer end of the insertion sleeve.

20. The insertion device as claimed in claim 11, wherein components thereof are manufactured from a biocompatible plastic.

21. The insertion device as claimed in claim 11, wherein at least the insertion sleeve follows a radius of curvature, particularly one which is adapted to a natural curvature of a urethra of a user.

22. The liquid catheter of claim 1, wherein the catheter body lies enclosed, and is worn wholly internally, within the cavity of the bladder in a rest position, and the catheter body is for evacuation of the bladder manipulatable transluminally in a proximal direction relative to the anchoring portion distally relative to the bladder.

23. A urinary catheter for insertion into a bladder of a female user, comprising:
a catheter body comprising i) an elongated shaft portion having a longitudinal liquid channel that passes a liquid flow between a distal side and a proximal side thereof, and ii) an anchoring portion located distally of said shaft portion, said anchoring portion comprising a deployable anchoring body, the anchoring body comprising plural resilient filaments connected and adjacent said shaft portion, said resilient filaments being sufficiently resilient to transform from a straightened state to a longitudinally curved state; and
an operating member extending proximally of said catheter body and being connected durably to said catheter body,
wherein said anchoring body is deployable from i) a relatively slender first state, said slender first state allowing a transluminal introduction of said catheter body in a cavity of the female bladder, into ii) an expanded second state, said expanded second state preventing inadvertent escape of the catheter body from said the cavity of the bladder,
wherein said shaft portion has a sufficient length that reaches beyond a closure point of a luminal sphincter when the anchoring body resides in the cavity of the bladder, and
wherein said catheter body is sufficiently compact to be received completely inside the cavity of the bladder,
wherein the anchoring body is self expandable from said slender first state into said expanded second state,
wherein said anchoring body is balloon shaped in said expanded second state and widens in a distal direction at a side directed towards said shaft portion, and
wherein a pull force applied to said operating member holds said resilient filaments in the straightened state, and a subsequent release of said operating member transforms said resilient filaments from the straightened state to the longitudinally curved state to thereby displace said catheter body from said urethral sphincter and into the cavity of the bladder.

24. The liquid catheter of claim 23, further comprising:
longitudinal incisions which mutually separate the resilient filaments in a peripheral direction, and
wherein said plural resilient filaments are linked, and
wherein the straightened state is unstable and the longitudinally curved state is stable.

25. The liquid catheter of claim 23, wherein the catheter body lies enclosed, and is worn wholly internally, within the cavity of the bladder in a rest position, and the catheter body is for evacuation of the bladder manipulatable transluminally in a proximal direction relative to the anchoring portion distally relative to the bladder.

* * * * *